United States Patent [19]

Christner et al.

[11] Patent Number: 5,346,606
[45] Date of Patent: Sep. 13, 1994

[54] ELECTROCHEMICAL SENSOR

[75] Inventors: Kurt W. Christner; Stewart Thoeni, both of Carson City, Nev.

[73] Assignee: Elsag International N.V., Amsterdam Zuidoost, Netherlands

[21] Appl. No.: 106,529

[22] Filed: Aug. 16, 1993

[51] Int. Cl.⁵ .............................. G01N 27/26
[52] U.S. Cl. ..................... 204/433; 204/435; 204/420; 204/153.21
[58] Field of Search ............ 204/433, 435, 420, 153.21

[56] References Cited

U.S. PATENT DOCUMENTS

| Re. 31,333 | 8/1983 | Barben | 324/450 |
|---|---|---|---|
| 3,440,525 | 4/1969 | Cardeiro | 324/30 |
| 4,664,772 | 5/1987 | Zaccari et al. | 204/433 |
| 4,913,793 | 4/1990 | Leonard | 204/433 |
| 5,147,524 | 9/1992 | Broadley | 204/433 |

Primary Examiner—John Niebling
Assistant Examiner—Bruce F. Bell
Attorney, Agent, or Firm—Michael M. Rickin; Paul R. Katterle

[57] ABSTRACT

An electrochemical sensor wherein the salt bridge is a unitary plug of semipermeable material which is saturated with an electrolyte. The plug has a spiral cut from its outer surface to the central bore of the plug. The spiral has at least one complete turn and starts at or near one end of the plug and stops at or near the other end of the plug. A layer of impermeable material is deposited in the plug to thereby form an ion impermeable spiral barrier.

16 Claims, 2 Drawing Sheets

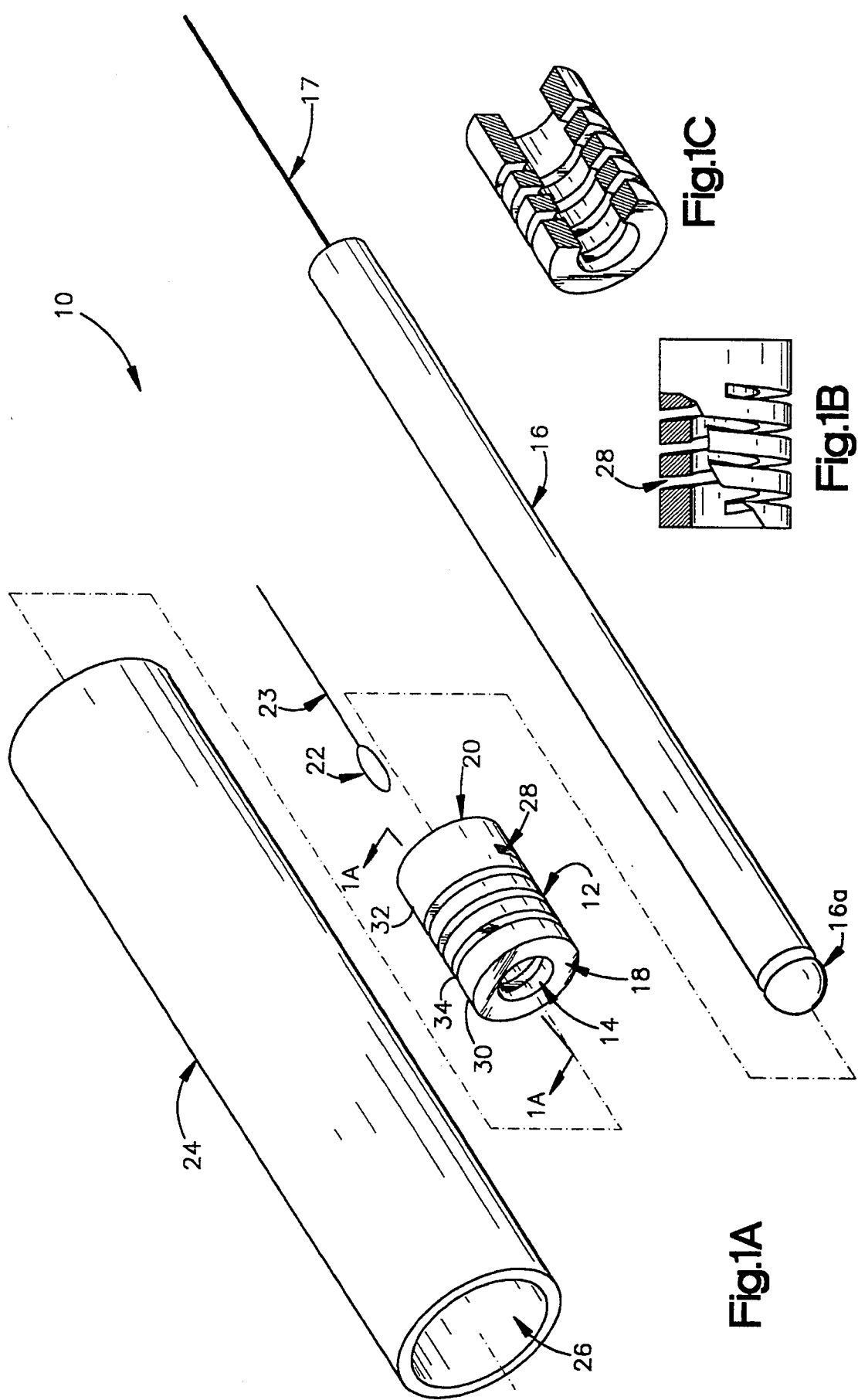

ELECTROCHEMICAL SENSOR

1. FIELD OF THE INVENTION

This invention relates to instruments for sensing the characteristics of a fluid, more particularly to electrochemical sensors and particularly, but not exclusively, to reference cells used in pH, ORP, or other specific ion sensors.

2. DESCRIPTION OF THE PRIOR ART

The reference cell used in pH, ORP, or other specific ion sensors typically utilizes a metal-metal salt (e.g., Ag/AgCl) element. Since this reference element must maintain a common electrical potential with the specimen fluid, a suitable electrolyte in the form of a salt solution links the element to the specimen fluid. This electrolyte provides the conductive, i.e., salt, bridge to the specimen fluid and surrounds the reference element with an electrochemically stable environment. The region where the electrolyte and the specimen fluid meet is called the liquid junction and usually takes the form of a porous material.

The ideal liquid junction would provide a conductive link to the specimen fluid and prevent any mixing of the specimen fluid with the electrolyte. Usually, mixing is unavoidable, which can cause undesirable effects. Thus, the liquid junction is typically the weakest point of a reference cell design.

Current liquid junction designs employ various porous material such as wood, Teflon, ceramic frits, wicks, ground glass joints, or even just a small hole. These junctions either separate the specimen fluid from a reservoir of electrolyte containing the reference element or are saturated with the electrolyte fluid and house the reference element in a location far removed from the specimen fluid.

A common problem with liquid junctions is maintaining a conductive path between the specimen fluid and the reference element. Liquid junctions with small openings can easily be plugged by solids contained within the specimen fluid or by crystallization of the specimen fluid with the electrolyte through some type of chemical reaction. To reduce plugging problems, large junction surfaces have been employed.

In U.S. Pat. No. 3,440,525 ("the '525 Patent") to Cardeiro, he discloses a liquid junction that employs a large junction surface created by a single wood or porous ceramic plug. The structures of these materials maintain electrolyte contact through small capillaries extending longitudinally between the specimen fluid and reference electrolyte. The liquid junction of the '525 Patent possesses a very high density of electrically conductive salt links to the specimen fluid via the capillary structure of the wood or ceramic plug.

Another common difficulty with reference cell designs is isolating the reference element from the specimen fluid. When the specimen fluid penetrates into the liquid junction or electrolyte reservoir and changes the electrolyte concentration, the potential produced by the reference cell begins to drift and can reach levels too large for calibration methods. If the specimen fluid reaches the reference element, poisoning of this element can occur, causing the reference potential to become unstable. Since these are undesirable effects, the design of the reference cell should minimize or eliminate the exchange of electrolyte with specimen fluid.

In U.S. Pat. No. Re. 31,333 ("the '333 Patent") to Barben, he discloses the use of multiple plugs of semipermeable material with longitudinal capillaries extending from one end of the plug to the other. These plugs are linked through a series of smaller plugs. The large plugs are sealed between successive plugs causing the ion transfer path to be linked longitudinally and transversely between each plug.

Similarly, U.S. Pat. No. 5,147,524 ("the '524 Patent") to Broadley discloses the use of a single plug of semipermeable material with longitudinal capillaries extending from one end of the plug to the other. A plurality of axially spaced notches are radially machined part way through the plug and filled with an ion impermeable material such as epoxy. The notches are alternately machined so the notch closest to the plug's open end is machined from one side of the plug, the next closest notch is machined from the other side of the plug, etc.

The notches are oriented at an oblique angle to the axis of the plug. The obliquely angled notch filled with the ion impermeable material is said to function as an ion trap. According to the '524 Patent, the angled notches are said to establish a plurality of traversal zones wherein ion migration is by capillary action, a plurality of transition zones wherein the ions must move laterally or radially into another traversal zone and a plurality of ion traps.

The present invention describes a reference half cell design that creates a tortuous path by forcing ion migration through the capillary walls of the semipermeable material. Therefore, the present invention provides a new reference cell design that greatly retards the flow of contaminating ions through the salt bridge by forcing the ion migration path to be extensively through the capillary walls of a semipermeable material having longitudinally oriented capillaries. Thus, an ion migration path is created that will greatly reduce the dilution of electrolyte within the reference cell and diminish the likelihood of poisoning the reference element.

SUMMARY OF THE INVENTION

The present invention describes a device for use in connection with measuring ionic properties in a specimen fluid. The device comprises a salt bridge. The salt bridge comprises an electrolyte-impregnated unitary semipermeable plug which has a central bore and a first end adapted to contact the specimen fluid; a second end opposite the first end; a longitudinal axis extending between the first and second ends; and an outer surface radially outward of the longitudinal axis.

The plug has a spiral cut in the outer surface which penetrates into the central bore. The spiral has at least one complete turn and starts at or near the first end and ends at or near the second end. An impermeable material is deposited in the spiral to substantially fill the spiral to thereby form an ion impermeable spiral barrier.

The invention describes an electrochemical sensor which comprises a reference electrode, a sensing electrode and a salt bridge. The salt bridge comprises a unitary plug made of semipermeable material and saturated with an electrolyte. The plug has a central axial bore for holding the sensing electrode therein. The plug has an outer surface and a first end and a second end between which the central bore extends. The plug also has a spiral cut in the outer surface which penetrates into the central axial bore. The spiral has at least one complete turn and starts at or near the first end and ends at or near the second end so that the spiral interrupts the direct axial capillary path from the first end to the second end.

The salt bridge also comprises a layer made of impermeable material deposited in the spiral. The first end of the plug and the sensing electrode are adapted to contact a specimen fluid to be measured and the second end of the plug is in electrochemical contact with the reference electrode. The entire plug serves to separate the reference electrode from the specimen fluid.

This invention characterizes a method for physically separating a reference electrode from a specimen fluid during measurement of the ionic properties of the fluid. The method comprises the step of interposing a salt bridge between the reference electrode and the specimen fluid. The salt bridge is formed of unitary semipermeable material having a central bore. The unitary material is impregnated with an electrolyte and has axially separated first and second ends and axially extending capillary passageways.

The method also comprises the step of inhibiting ion transfer through the passageways by providing in the salt bridge a spiral cut penetrating into the central bore. The spiral cut has at least one complete turn and starts at or near the first end of the plug and ends at or near the second end of the plug. The spiral cut extends transversely across the capillary passageways but not all the way through the salt bridge so that the spiral cuts through substantially all of the capillary passageways. A layer of impermeable material is provided in the spiral to inhibit ion transfer longitudinally in the axially extending capillary passageways and allow ion flow only transversely through the capillary walls of the semipermeable material.

The invention constitutes an electrochemical sensor which comprises a unitary semipermeable plug impregnated with an electrolyte. The plug has a central bore and axially separated first and second ends and functions as a salt bridge. The sensor also comprises a sensing electrode positioned at the first end and adapted to contact a specimen fluid. The sensor further comprises a reference electrode positioned at the second end and a spiral cut in the surface of the plug. The spiral penetrates into the central bore. The spiral has at least one complete turn and starts at or near the first end and ends at or near the second end and is filled with an impermeable material.

DESCRIPTION OF THE DRAWING

FIG. 1a shows a sensor in accordance with the present invention.

FIG. 1b and 1c show a section along line A—A and an isometric half section of the plug of the sensor shown in FIG. 1a.

FIG. 2b shows a sensor embodied in accordance with the teachings of the '524 Patent having the same predetermined number of plug means as the sensor of FIG. 2a.

FIG. 2c shows a sensor embodied in accordance with the present invention having the same predetermined number of plug means as the sensor of FIG. 2a.

DESCRIPTION OF THE PREFERRED EMBODIMENT

Figure 2C:
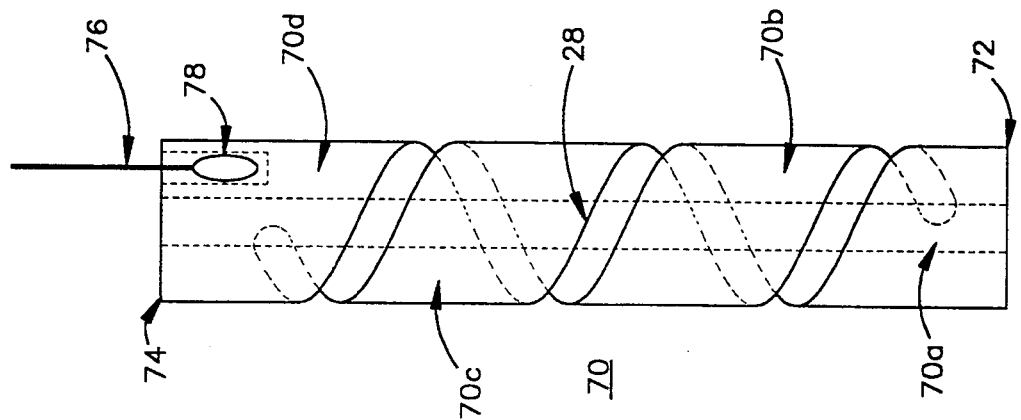

Referring now to FIG. 1a, there is shown, in accordance with the present invention, an embodiment for a sensor 10 for measuring pH, ORP or specific ions in a specimen fluid. For ease of description, the embodiment of the sensor shown in FIG. 1a will be referred to hereinafter as a "sensor." The sensor includes a cylindrical plug 12 fabricated from a porous material such as wood wherein the capillaries run in the direction of the axis of the plug. The plug is saturated, i.e., impregnated, with an appropriate electrolyte such as a saturated salt solution.

Plug 12 has a central longitudinal bore 14 for receiving therein a measurement or sensing electrode 16 that has an electrical lead 17 for attachment to a suitable device, for example, a pH meter (not shown), which can process the signal generated by sensor 10. The plug has a first end 18 through which the bulb 16a of the measurement electrode protrudes when the sensor is assembled. The plug has a second end 20 to which an insulating plug (not shown) is attached to prevent seepage of the electrolyte into the region (not shown) where the electrical connection is made with lead 17 and a coaxial cable or equivalent (not shown) to a suitable device, for example, a pH meter.

The sensor includes a reference electrode or element 22 that has an electrical lead 23 which is also connected to the coaxial cable or equivalent (not shown). As is well known to those skilled in the art and as is shown in FIG. 2 of the '333 Patent and FIG. 2 of the '524 Patent, the plug may include a cavity (not shown) in the second end 20 for receiving the reference element 22. The sensor further includes a nonconductive cylindrical elongated housing 24 that has a central bore 26 therein for receiving plug 12. Housing 24 may be constructed in such a manner as to allow for engagement into a complementary fitting mounted onto a pipe, tank or other vessel that holds the specimen fluid.

As can be appreciated from FIG., 1a, the plug 12 holds both the measurement electrode 16 and the reference electrode 22. The bulb 16a of the measurement electrode 16 can be immersed in the specimen fluid while the reference electrode 22 is separated from the specimen fluid by the structure of plug 12. This separation reduces the migration of the specimen fluid to the reference electrode to thereby reduce the poisoning of that electrode by contaminating ions. As can further be appreciated from FIG. 1a, the electrical circuit of sensor 10 is completed by establishing electrical communication through the electrolyte-impregnated plug 12 between the reference electrode 22 and the specimen fluid in which the bulb 16a of measurement electrode 16 is immersed.

As is shown in FIGS. 1a, 1b, and 1c a spiral cut 28 is machined in the plug starting at or near the first end 18 and continuing to or near the second end 20. The spiral cut 28 penetrates completely through the wood structure of the plug and into the central longitudinal bore 14. The spiral cut 28 is perpendicular to the length of the plug. The spiral cut is filled (not shown) with an electrically nonconductive, ion impermeable material, such as epoxy, to prevent direct communication between the capillaries on either side of the spiral cut, thus forming a nonconductive spiral barrier. As will be described in more detail below, the spiral barrier further reduces the migration of ions between the reference electrode 22 and the specimen fluid in which bulb 16a of measurement electrode 16 is immersed. While a spiral cut 28 of more than three complete turns is shown in FIG. 1a, it should be appreciated that the spiral cut should have at least more than one complete turn.

The spiral barrier divides the plug 12 into a first region 30 and a second region 32. The first region 30 is that part of the plug between the beginning of the spiral barrier at or near the first end 18 and that location 34 on the surface of the plug wherein the spiral barrier has completed its first 360 degrees. The second region is that part of the plug between location 34 and the end of the spiral barrier at or near second end 20.

In the first region 30 ions migrate along the capillaries until the ions reach the epoxy-filled spiral cut that acts as a barrier to further capillary migration. The distance that an ion migrates along the capillaries in the first region is dependent on where on first end 18 the ion enters the plug. An ion that enters the first end just before the beginning of the spiral barrier will migrate the furthest distance in the first region along the capillaries.

When an ion in the first region reaches the barrier formed by the epoxy-filled spiral cut, the ion must seek a new migration path. This new path will be through the semipermeable membranes of the cell walls in the wooden plug. Once the ions in the first region reach the spiral barrier, the ions will then migrate transversely through the semipermeable membranes along the spiral barrier. Starting in the first region and continuing through the second region, the spiral barrier thus establishes a circuitous path for ion transfer.

It should be appreciated that ion migration along the capillaries can only occur in the first region of plug 12. It should further be appreciated that when ions migrating along the capillaries first encounter the spiral barrier, the migration of the ions takes place thereafter through a circuitous path established through the semipermeable membranes of the cell walls in the plug 12. Further it should be appreciated that, since ion transport through these membranes is much more difficult than transport through the capillaries, the life of the reference cell and therefore the sensor will be significantly improved as it is the transport of ions into and out of the reference cell that leads to dilution of the electrolyte and poisoning of the reference cell. Additionally, it should be appreciated that the circuitous path can easily be lengthened by increasing the number of complete turns in the spiral. Thus, a much shorter plug will have the same or improved life as compared with prior art reference cells.

It should also be appreciated that the diameter of bore 14 is selected to accommodate electrode 16. As the bore diameter is increased, the transverse migration path per turn of the spiral is increased. Increasing the diameter of the bore decreases the cross sectional area of the transverse path, which increases the impedance of the reference. Any negative effect that such increased reference impedance may have on the measurement can be accommodated by well known electronic circuit techniques.

Figure 2B:
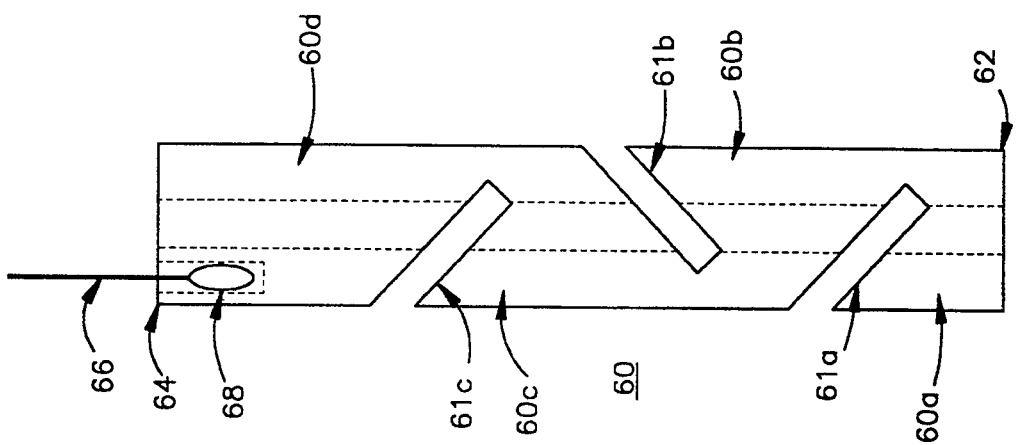
Figure 2A:
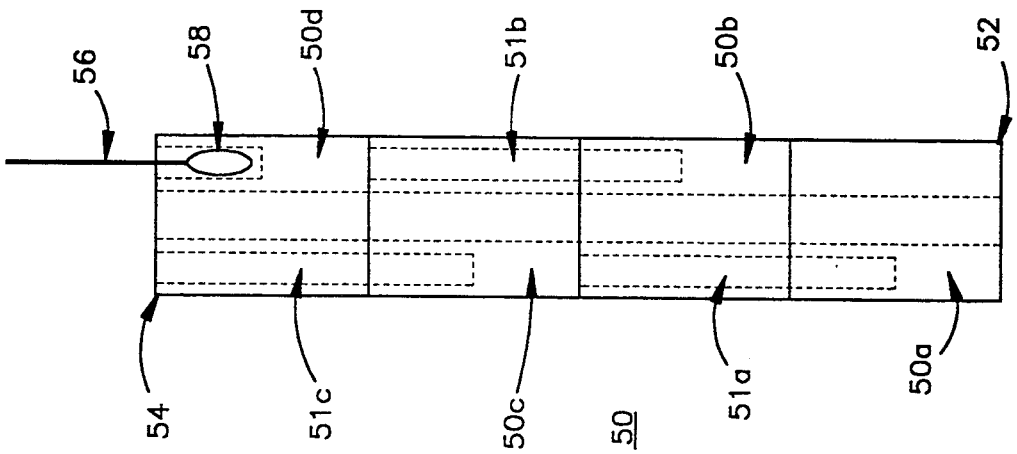
FIG. 2a shows a sensor embodied in accordance with the teachings of the '333 Patent and having a predetermined number of plug means.

Referring now to FIGS. 2a, b and c there are shown plugs 50, 60 and 70 embodied, respectively, in accordance with the teachings of the '333 Patent, the '524 Patent and of the present invention. For ease of comparison each of the plugs 50, 60 and 70 can be thought of as divided into four plug means 50a to 50d between first end 52 and second end 54 for plug 50, four plug means 60a to 60d between first end 62 and second end 64 for plug 60, and four plug means 70a to 70d between first end 72 and second end 74 for plug 70. Each of the plugs 50, 60 and 70 have a reference electrode 56, 66 and 76 in a cavity 58, 68 and 78 in the associated second end 54, 64 and 74.

Each of the plugs 50, 60 and 70 support primarily longitudinal migration or transport of ions in plugs means 50a, 60a and 70a. In accordance with the teachings of the '333 and '524 Patents, plugs 50 and 60 support longitudinal and transverse migration or transport of ions in plug means 50b to 50d and 60b to 60d. As is taught in the '333 Patent, the longitudinal migration or transport of ions in plug means 50b to 50d of plug 50 occurs only in rods or dowels 51a, 51b and 51c. As is taught in the '524 Patent, the epoxy-filled obliquely angled notches 61a, 61b and 61c comparably cause transverse migration or transport of ions in plug means 60b, 60c and 60d of plug 60.

In accordance with the present invention and as was described in connection with FIG. 1a and 1b, the epoxy-filled spiral cut 28 in plug 70 completely blocks longitudinal transport or migration of ions in plug means 70b, 70c and 70d. Therefore, the epoxy-filled spiral cut 28 only permits transverse migration or transport of ions in plug means 70b, 70c and 70d.

From FIGS. 2a to 2c and the above explanation, it can be seen that a plug embodied in accordance with the present invention shown in FIG. 1a will have a much longer distance of transverse migration or transport of ions than a plug embodied in accordance with the '333 or '524 Patents. The transverse migration in each plug means from 50b to 50d is only 180° for each means, and the transverse migration for 60b to 60d is less than 180° for each means. Conversely, the transverse migration in plug means 70b to 70c is 360° for each means and up to 180° for plug means 70d. From FIGS. 2a to 2c and the above explanation, it can also be seen that in a sensor embodied in accordance with the present invention increasing the number of turns in the spiral cut 28 for the same plug length will increase the distance wherein transverse migration or transport of ions occurs.

One method of manufacturing sensor 10 is to first soak plug 12 in a saturated aqueous solution of the desired electrolyte such as potassium chloride. Thereafter the longitudinal bore 14, the spiral cut 28 and the cavity for the reference electrode are machined in plug 12. Alternatively, the plug can be soaked in the saturated aqueous solution either after the machining described above has taken place and the reference electrode is epoxy bonded to the wall of its cavity or after the epoxy resin in the spiral cut 28 and any other epoxy resin associated with the sensor has hardened. The techniques used to assemble the sensor are well known to those skilled in the art and may include the positioning of a porous disc, with or without O-rings (not shown), onto first end 18 to establish a liquid junction between plug 12 and the specimen fluid and the use of an epoxy resin (not shown) disposed between plug 12 and housing 24.

It is to be understood that the description of the preferred embodiment is intended to be only illustrative, rather than exhaustive, of the present invention. Those of ordinary skill will be able to make certain additions, deletions, and/or modifications to those embodiments of the disclosed subject matter without departing from the spirit of the invention or its scope, as defined by the appended claims.

What is claimed is:

1. A device for use in connection with measuring ionic properties in a specimen fluid, which comprises:

(a) a salt bridge comprising an electrolyte-impregnated unitary semipermeable plug having
  (i) a central bore and a first end adapted to contact the specimen fluid,
  (ii) a second end opposite the first end,
  (iii) a longitudinal axis extending between said first end and said second end, and
  (iv) an outer surface radially outward of said longitudinal axis,
wherein said plug has a spiral cut in said outer surface and penetrating into said central bore, said spiral having at least one complete turn and starting at or near said first end and ending at or near said second end; and
  (b) an impermeable material deposited in said spiral to substantially fill said spiral thereby forming an ion impermeable spiral barrier.

2. The device of claim 1 wherein said semipermeable plug is wood impregnated with an electrolyte.

3. The device of claim 1 wherein said impermeable material is epoxy.

4. The device of claim 1 further comprising a housing for closely receiving said plug therein.

5. The device of claim 4 further comprising a reference electrode in electrochemical connection with said plug first end and physically separated from direct communication from said specimen fluid by said plug.

6. The device of claim 5 further comprising a sensing electrode in said housing.

7. The device of claim 6 wherein said sensing electrode extends axially through said plug and protrudes outwardly from said first end and said device further comprises a cavity formed in said plug second end in which said reference electrode is located.

8. An electrochemical sensor, comprising:
  (a) a reference electrode;
  (b) a sensing electrode;
  (c) a salt bridge comprising a unitary plug made of semipermeable material and saturated with an electrolyte,
    (i) said plug having a central axial bore for holding said sensing electrode therein,
    (ii) said plug having an outer surface and a first end and a second end between which said central axial bore extends and
    (iii) having a spiral cut in said outer surface and penetrating into said central axial bore, said spiral having at least one complete turn and starting at or near said first end and ending at or near said second end so that said spiral interrupts the direct axial capillary path from said first end to said second end; and
  (d) a layer made of impermeable material deposited in said spiral, wherein said first end of said plug and said sensing electrode are adapted to contact a specimen fluid to be measured, and said second end of said plug is in electrochemical contact with said reference electrode and serves to separate said reference electrode from said specimen fluid.

9. The electrochemical sensor of claim 8 wherein said semipermeable material is wood impregnated with an electrolyte.

10. The electrochemical sensor of claim 8 wherein said impermeable material is epoxy.

11. The electrochemical sensor of claim 8 further comprising a housing for receiving said plug therein.

12. The electrochemical sensor of claim 11 wherein said sensing electrode protrudes outwardly from said first end.

13. A method for physically separating a reference electrode from a specimen fluid during measurement of the ionic properties of said fluid, comprising the steps of:
  (a) interposing a salt bridge between said reference electrode and said specimen fluid, wherein said salt bridge is formed of unitary semipermeable material having a central bore, said unitary material impregnated with electrolyte and has axially separated first and second ends and axially extending capillary passageways; and
  (b) inhibiting ion transfer through said passageways by providing in said salt bridge a spiral cut penetrating into said central bore and having at least one complete turn and starting at or near said first end and ending at or near said second end extending transversely across said capillary passageways but not all the way through said salt bridge, so that said spiral cuts through substantially all of said capillary passageways, wherein a layer of impermeable material is provided in said spiral to inhibit ion transfer longitudinally in said axially extending capillary passageways and allows ion flow only transversely through the capillary walls of said unitary semipermeable material.

14. An electrochemical sensor, comprising:
  (a) a unitary semipermeable plug impregnated with an electrolyte, said plug having a central bore and axially separated first and second ends and functioning as a salt bridge;
  (b) a sensing electrode positioned at said first end and adapted to contact a specimen fluid;
  (c) a reference electrode positioned at said second end; and
  (d) a spiral cut in the surface of said plug and penetrating into said central bore, said spiral having at least one complete turn and starting at or near said first end and ending at or near said second end and filled with an impermeable material.

15. The electrochemical sensor of claim 14 wherein said unitary semipermeable plug is wood impregnated with an electrolyte.

16. The electrochemical sensor of claim 14 wherein said impermeable material is epoxy.

* * * * *